United States Patent
Mamine et al.

(10) Patent No.: US 7,718,129 B2
(45) Date of Patent: May 18, 2010

(54) BIOASSAY SUBSTRATE AND BIOASSAY DEVICE AND METHOD

(75) Inventors: Takayoshi Mamine, Kanagawa (JP); Yasuhiro Sakamoto, Kanagawa (JP); Motohiro Furuki, Tokyo (JP); Isamu Nakao, Tokyo (JP)

(73) Assignee: Sony Corporation, Tokyo (JP)

( * ) Notice: Subject to any disclaimer, the term of this patent is extended or adjusted under 35 U.S.C. 154(b) by 512 days.

(21) Appl. No.: 10/559,745

(22) PCT Filed: Jun. 10, 2004

(86) PCT No.: PCT/JP2004/008476
§ 371 (c)(1),
(2), (4) Date: Dec. 7, 2005

(87) PCT Pub. No.: WO2004/111620
PCT Pub. Date: Dec. 23, 2004

(65) Prior Publication Data
US 2006/0128030 A1    Jun. 15, 2006

(30) Foreign Application Priority Data
Jun. 10, 2003 (JP) .............................. 2003-165516

(51) Int. Cl.
*G01N 21/00* (2006.01)
(52) U.S. Cl. .................. 422/82.05; 422/50; 422/61; 422/63; 422/64; 422/68.1; 422/82.06; 422/82.08; 435/7.1; 435/283.1; 435/287.1; 435/288.7
(58) Field of Classification Search .............. 422/50, 422/61, 63, 64, 68.1, 82.05, 82.06, 82.08; 435/7.1, 283.1, 287.1, 288.7
See application file for complete search history.

(56) References Cited

U.S. PATENT DOCUMENTS

| 6,143,247 A | * | 11/2000 | Sheppard et al. | ............... 422/63 |
| 6,302,134 B1 | * | 10/2001 | Kellogg et al. | ................ 137/74 |
| 6,319,468 B1 | * | 11/2001 | Sheppard et al. | ............... 422/63 |
| 6,327,031 B1 | * | 12/2001 | Gordon | ....................... 356/72 |
| 6,965,433 B2 | * | 11/2005 | Zoval et al. | ................ 356/445 |

(Continued)

FOREIGN PATENT DOCUMENTS

JP    2-232563    9/1990

(Continued)

*Primary Examiner*—Melanie Yu
(74) *Attorney, Agent, or Firm*—Finnegan, Henderson, Farabow, Garrett & Dunner, L.L.P.

(57) ABSTRACT

A bioassay substrate (1) takes a flat-plate shape in which the principal surface similar to that of optical disc such as CD, etc. is circular. At the center of the substrate (1), there is formed a center hole (2) into which a chucking mechanism for rotation and holding is inserted. The substrate (1) is rotationally driven with the center hole (2) being as center. On the substrate (1), there are formed two regions of a recording region (3) and a reaction region (4) which are formed in concentrical form in a radial direction. The recording region (3) is a region where, similarly to the optical disk information recording medium, laser beams are irradiated so that recording/reproduction of information is optically performed. The reaction region (4) is a region serving as the filed of mutual reaction between probe DNA (nucleotide chain for detection) and sample DNA (marked or labeled nucleotide chain), in concrete terms, the field of hybridization reaction.

2 Claims, 4 Drawing Sheets

U.S. PATENT DOCUMENTS

| | | | |
|---|---|---|---|
| 2001/0016316 A1* | 8/2001 | Virtanen | 435/6 |
| 2002/0168652 A1* | 11/2002 | Werner et al. | 435/6 |
| 2003/0059803 A1* | 3/2003 | Werner et al. | 435/6 |

FOREIGN PATENT DOCUMENTS

| | | |
|---|---|---|
| JP | 2-269938 | 11/1990 |
| JP | 3-225278 | 10/1991 |
| JP | 4-233462 | 8/1992 |
| JP | 5-5741 | 1/1993 |
| JP | 10-504397 | 4/1998 |
| JP | 2001-238674 | 9/2001 |
| JP | 2002-501174 | 1/2002 |
| JP | 2002-250726 | 9/2002 |
| JP | 2004-93415 | 3/2004 |

* cited by examiner

BIOASSAY SUBSTRATE AND BIOASSAY DEVICE AND METHOD

This application claims the benefit of priority to Japanese Patent Application No. 2003-165516, filed on Jun. 10, 2003, the entire contents of which are incorporated herein by reference.

TECHNICAL FIELD

The present invention relates to a substrate for bioassay, e.g., DNA chip, etc., and a bioassaying apparatus adapted for performing bioassay by using substrate for bioassay. More particularly, the present invention relates to a substrate for bioassay in which reaction region serving as a field of mutual reaction between probe material and sample material is formed, and a bioassaying apparatus and a bioassaying method which are adapted for detecting fluorescence produced from fluorescence marking agent existing in the reaction region.

BACKGROUND ART

At present, substrates for bioassay which are so-called DNA chip or DNA micro-array (hereinafter generally called DNA chip) in which predetermined DNA substances are finely arranged by the micro-array technology are utilized for mutation of gene, SNPs (monobasic polytype) analysis, and/or gene manifestation frequency analysis, etc., and begin to be widely utilized in production of medicine, clinical diagnosis, pharmacologic genomics, legal medicine and/or other fields.

In such DNA chips, since a large number of various DNA oligonucleotide chains or cDNA (complementary DNA) substances, etc. are arranged on glass substrate or silicon substrate, inclusive analysis of mutual reaction between materials such as hybridization, etc. can be performed.

In the DNA analysis technique using DNA chip, there is employed an approach to PCR (Polymerase Chain Reaction)-amplify mRNA (messenger RNA) extracted from cell and/or tissue, etc., while assembling fluorescence probe dNTP by inverse transfer PCR, etc. with respect to, e.g., probe DNA which has been changed into solid-phase state (immobilized) on DNA chip to produce sample DNA to drop the sample DNA onto the DNA chip to perform hybridization of hybridization of probe DNA and sample DNA to perform fluorescent measurement by a predetermined detector.

Here, e.g., in the Japanese Patent Application Laid Open No. 2001-238674 publication and the PCT Patent Application Laid Open No. 2002-501174 publication, it is proposed that the shape of the DNA chip is caused to have circular-plate shape to apply substrate technology cultivated in the filed of optical disc to the DNA analysis.

In the case of performing DNA analysis to which the technology of the optical disc has been applied, there can be applied such a servo technology to detect, by light detector, fluorescence produced from fluorescence mark while rotating the DNA chip caused to have circular-plate shape to specify light emitting position of that fluorescence by the addressing technology. Thus, increase in the number of sample materials to be processed and improvement in detection accuracy and detection speed can be performed.

However, in the conventional DNA chip technologies, since the number of integration times and integration density of the DNA chip itself were small, it cannot be said that quantity of analysis which can be attained by single assay is sufficient. As a result, user was difficult to freely set the kind and the number of materials to be detected, and classification of arrangements (grouping) on the substrate used.

In addition, in the conventional analysis technique using DNA chip, information of kind or grouping of material to be detected of DNA chip, analyzed result by the DNA chip and analysis program for DNA chip, etc. were used in the state separately recorded with respect to different information recording media. For this reason, association between DNA chip and information recording medium where analysis results, etc. are recorded is weak. As a result, it was difficult to integrally perform management of DNA chip and information.

DISCLOSURE OF THE INVENTION

An object of the present invention is to provide a substrate for assay which is adapted to have ability to handle information in more variety manner, and to provide a bioassaying apparatus and a bioassaying method which are adapted for performing bioassay by using such a substrate for bioassay.

The substrate for bioassay according to the present invention is directed to a substrate for bioassay in which bioassay based on mutual reaction between probe material and sample material is performed, the bioassay substrate being constituted so as to have flat-plate shape, the bioassay substrate including: a reaction region adapted so that the sample material and fluorescence marking agent are permitted to be dropped from the upper side and the probe material is permitted to be immobilized, the reaction region serving as a field of mutual reaction between the probe material and the sample material, and being such that plural wells to which fluorescence with respect to the fluorescence marking agent is irradiated from the lower side are formed; and an information region where light is irradiated from the lower side to thereby have ability to record and/or reproduce information.

The bioassay substrate includes the reaction region where mutual reaction between materials is caused to take place, and the information region where signals are to be recorded.

The bioassaying apparatus according to the present invention is directed to a bioassaying apparatus adapted for performing bioassay based on mutual reaction between probe material and sample material, which comprises: substrate holding means for holding and rotationally driving a substrate for bioassay, the bioassay substrate including a reaction region adapted so that the sample material and fluorescence marking agent are permitted to be dropped from the upper side and the probe material is permitted to be immobilized, the reaction region serving as a field of mutual reaction between the probe material and the sample material, and being such that plural wells to which fluorescence with respect to the fluorescence marking agent is irradiated from the lower side are formed, and an information region where light is irradiated from the lower side to thereby have ability to record and/or reproduce information; a fluorescence detection optical system for irradiating fluorescence having a predetermined wavelength with respect to the reaction region of the bioassay substrate to detect presence or absence of the fluorescence having the predetermined wavelength produced from the fluorescence marking agent in accordance with the fluorescence; and an information recording/reproducing optical system for irradiating light having a predetermined wavelength with respect to the information region of the bioassay substrate to perform recording and/or reproducing operations of information on the basis of a reflected light thereof.

In the bioassaying apparatus, bioassay based on mutual reaction between materials is performed with respect to the bioassay substrate including the reaction region where mutual reaction between materials is caused to take place, and the information region where signals are to be recorded, and recording and/or reproducing operations of information are performed with respect thereto.

The bioassaying method according to the present invention is directed to a bioassaying method of performing bioassay based on mutual reaction between probe material and sample material, which comprises: holding and rotationally driving a substrate for bioassay, the bioassay substrate including a reaction region adapted so that the sample material and fluorescence marking agent are permitted to be dropped from the upper side and the probe material is permitted to be immobilized, the reaction region serving as a field of mutual reaction between the probe material and the sample material, and being such that plural wells to which fluorescence with respect to the fluorescence marking agent is irradiated from the lower side are formed, and an information region where light is irradiated from the lower side to thereby have ability to record and/or reproduce information; irradiating light having a predetermined wavelength with respect to the information region of the bioassay substrate to perform recording and/or reproducing operations of information on the basis of a reflected light thereof; and irradiating fluorescence having a predetermined wavelength with respect to the reaction region of the bioassay substrate to detect presence or absence of the fluorescence having the predetermined wavelength produced from the fluorescence marking agent in accordance with the fluorescence.

In the bioassaying method, bioassay based on mutual reaction between materials is performed with respect to the bioassay substrate including the reaction region where mutual reaction between materials is caused to take place, and the information region where signals are to be recorded, and recording and/or reproducing operations of information are performed with respect thereto.

BEST MODE FOR CARRYING OUT THE INVENTION

Explanation will now be given, as practical embodiment to which the present invention is applied, in connection with a bioassay substrate for DNA analysis to which the present invention is applied, and a bioassaying apparatus adapted for performing DNA analysis by using such a bioassay substrate. It should be noted that, in this Application, "bioassay" means biochemical analysis based on hybridization or other mutual reaction between materials.

(Bioassay Substrate)

Figure 1:
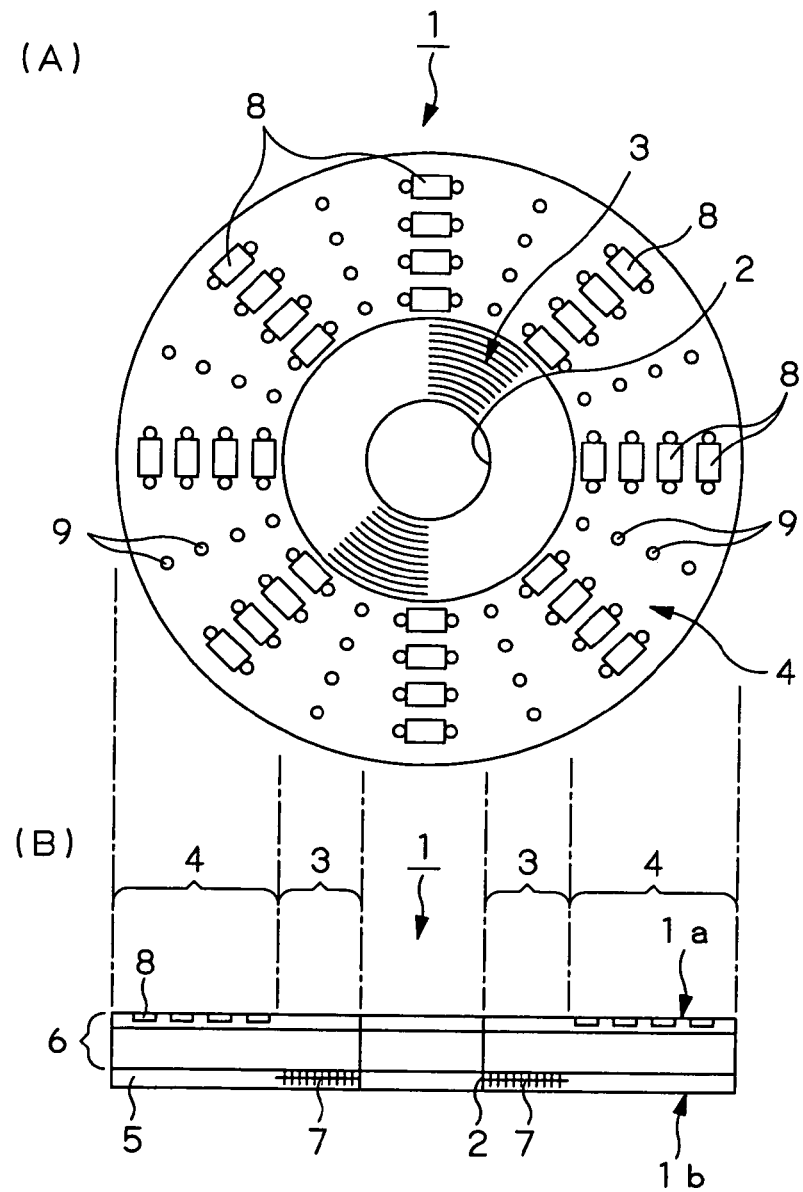
FIG. 1 is a plan view and a cross sectional view of a bioassay substrate of the embodiment of the present invention.

The view representing, in a model form, top view (FIG. 1(A)) and cross section (FIG. 1(B)) of bioassay substrate 1 of the embodiment of the present invention is shown in FIG. 1.

The bioassay substrate 1 takes flat-plate shape in which its principle surface similar to that of optical disk, e.g., CD (Compact Disk), DVD (Digital Versatile Disk), etc. is circular. Moreover, at the center of circle of the bioassay substrate 1, there is formed a center hole 2. A chucking mechanism for holding and rotating the bioassay substrate 1 when the bioassay substrate 1 is loaded (attached) into the DNA analyzer is inserted into the center hole 2.

The circular principal surface of the bioassay substrate 1 is divided, as shown in FIG. 1(A), into two regions of a recording region 3 and a reaction region 4 which are formed concentrically in radial direction. In this example, the recording region 3 is located at the inner circumferential side, and the reaction region 4 is located at the outer circumferential side. The recording region 3 may be located at the outer circumferential side, and the reaction region 4 may be located at the inner circumferential side. The recording region 3 is a region in which, similarly to the optical disk information recording medium, laser beams are irradiated so that recording/reproduction of information is optically performed. The reaction region 4 is a region serving as a field of mutual reaction between probe DNA (nucleotide chain for detection) and sample DNA (marked or labeled nucleotide chain), in concrete terms, a filed of hybridization reaction therebetween.

The layered structure of the bioassay substrate 1 is formed by an information layer 5 and a DNA layer 6 as shown in FIG. 1(B). Here, it is assumed that the information layer 5 is located at the lower layer, and the DNA layer 6 is located at the upper layer. Moreover, it is assumed that the surface of the DNA layer 6 side of the bioassay substrate 1 is referred to as top surface 1a, and the surface of the information recording layer 5 side thereof is referred to as lower surface 1b.

At the information layer 5, a signal recording film 7 to which laser beams are irradiated so that reproduction or recording/reproduction of data is performed, e.g., pits or phase change material, etc. is formed in the plane surface region corresponding to the recording region 3. Such a signal recording film 7 can be formed by a disk preparation method similar to that of optical disk such as CD (Compact Disk) or DVD (Digital Versatile Disk), etc.

Laser beams are irradiated from the lower surface 1b side of the bioassay substrate 1 to the signal recording film 7 so that reproduction or recording/reproduction of signals is performed. Moreover, the information layer 5 is formed by material which permits rays of light having wavelengths of fluorescence and control light irradiated at the time of DNA analysis, and fluorescence emitted from fluorescence marking agent at the time of DNA analysis to be transmitted therethrough. For example, the information layer 5 is formed by material such as quartz glass, silicon, polycarbonate or polystyrene, etc. It is to be noted that the details of fluorescence and control light which are irradiated, and fluorescence emitted will be described later.

Figure 2:
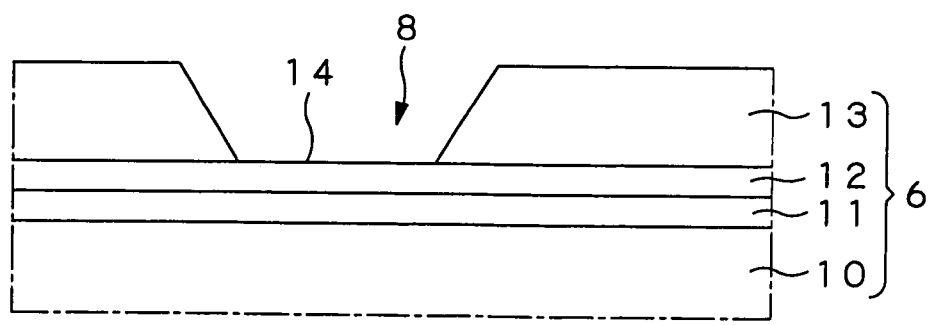
FIG. 2 is a cross sectional view showing layered structure of DNA layer of the bioassay substrate.

As shown in FIG. 2, the DNA layer 6 is a layered structure formed by a base layer 10, a transparent electrode layer 11, a solid-phase layer 12, and a layer 13 where wells are to be formed (hereinafter simply referred to as well formation layer as occasion may demand) from the lower layer side (i.e., from information layer 5 side).

The base layer 10 is material which permits rays of light having wavelengths of fluorescence and control light which are irradiated, and fluorescence emitted to be transmitted therethrough of which detail will be described later. For example, the base layer 10 is formed by material such as quartz glass, silicon, polycarbonate or polystyrene, etc.

The transparent electrode layer 11 is a layer formed on the base layer 10. The transparent electrode layer 11 is formed by material having light transmission characteristic and having conductivity, e.g., ITO (Indium-Tin-Oxide). The transparent electrode layer 11 is formed, as film, on the base layer 10 by, e.g., sputtering or electron beam evaporation, etc. so that it has thickness of about 250 nm.

The solid-phase layer 12 is a layer formed on the transparent electrode layer 11. The solid-phase layer 12 is formed by material for allowing one end of the probe DNA to be in solid-phase state. In this example, the solid-phase layer 12 is a layer in which $SiO_2$ of which surface can be modified by silane is formed, as film, by, e.g., sputtering or electron beam evaporation so that it has a thickness of about 50 nm.

The well formation layer 13 is a layer formed on the solid-phase layer 12. The well formation layer 13 is a layer where plural wells 8 for producing hybridization reaction between probe DNA and sample DNA are formed. The well is caused to have recessed-shape such that the top face 1a of the bioassay substrate 1 is opened, and has depth and dimensions such that solution in which sample DNA is included can be reserved or maintained when that solution, etc. is dropped. For example, the well 8 is formed so as to have dimensions in which the opening portion has dimensions of 100 μm×100 μm in length and breadth directions, and depth is caused to have about 5 μm. The solid-phase layer 12 is exposed to a bottom surface 14 thereat. Such well formation layer 13 is formed, e.g., by coating photosensitive polyimide on the solid-phase layer 12 by spin-coat, etc. so that it has a thickness of about 5 μm to expose and develop the coated photosensitive polyimide by using photo-mask in a predetermined pattern.

Figure 3:
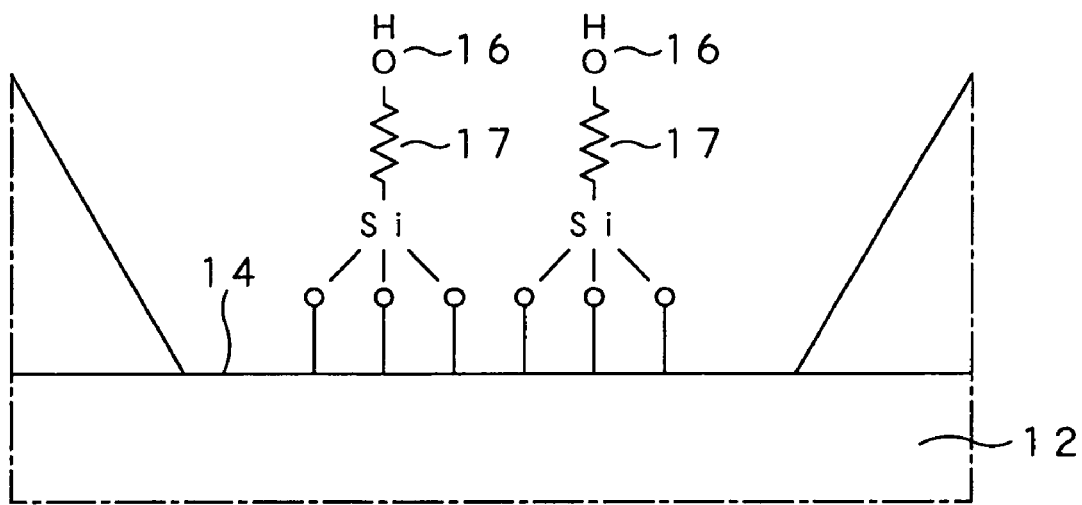
FIG. 3 is a view showing silane molecules having OH group modified on the bottom surface of well.
Figure 4:
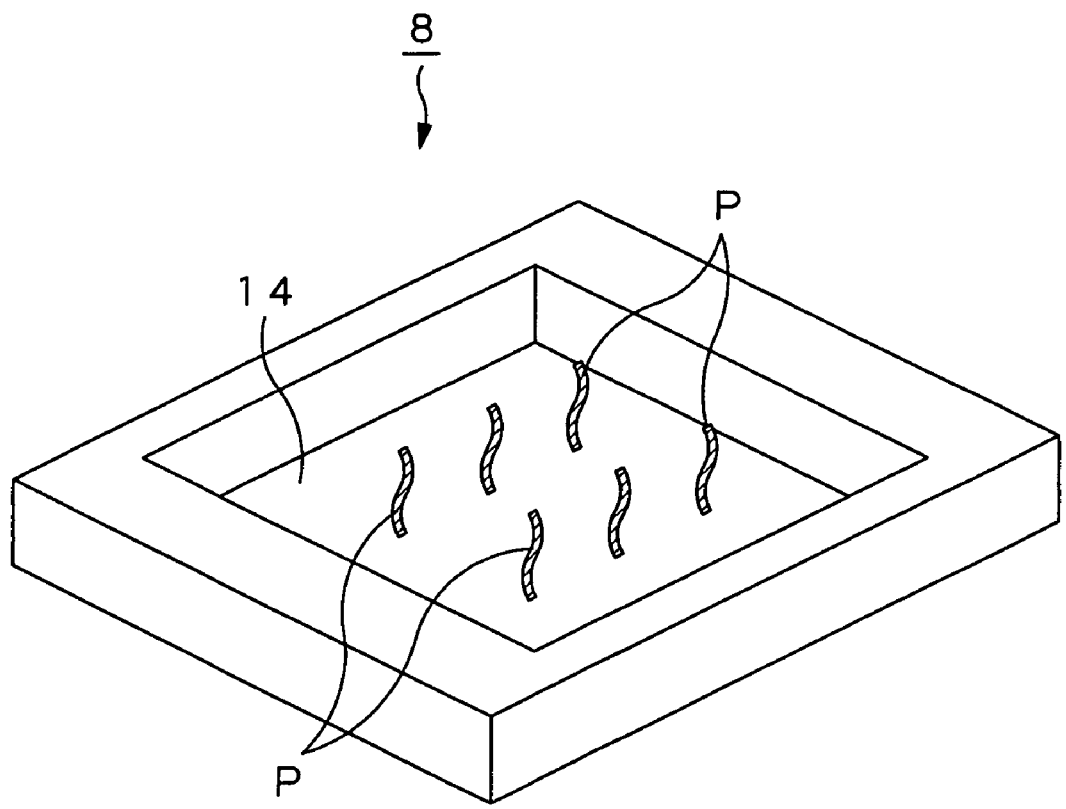
FIG. 4 is a view showing probe DNA bonded onto the bottom surface of well.

Further, at the well 8, in order that probe DNA of which one end is modified by functional group is bonded to the bottom surface 14 (the portion where the solid-phase layer 12 is exposed), the bottom surface 14 is surface-modified by the functional group. For example, at the well 8, as shown in FIG. 3, the bottom surface 14 (solid-phase layer 12 formed from $SiO_2$) is surface-modified by silane molecules 17 having OH groups 16. For this reason, probe DNA of which one end thereof is modified by, e.g., NCO group can be bonded to the bottom surface 14 of the well 8. As stated above, in the bioassay substrate 1, since one end of the probe DNA can be bonded to the bottom surface 14 of the well 8, probe DNA (P) substances can be bonded in order that chains are extended in a vertical direction from the bottom surface 14 as shown in FIG. 4.

Moreover, in the bioassay substrate 1, as shown in FIG. 1, plural wells 8 are disposed in the state equidistantly arranged at interval of, e.g., about 400 μm on radially plural columns in outer circumferential direction from the center of the principal surface. It is to be noted that, in this example, the plane surface region where wells 8 are formed is the range of the reaction region 4.

Further, at the bioassay substrate 1, laser beams are irradiated from the lower surface 1b side of the bioassay substrate 1 so that readable address pits 9 are formed. The address pits 9 are information for specifying positions of respective wells 8 on the plane surface of the bioassay substrate 1. By optically reading information from the address pits 9, it becomes possible to specify well 8 of the position where laser beams are irradiated at present among plural existing wells 8. Resulting from the fact that such address pits 9 are provided, it is possible to perform control of drop position of solution by the dropping unit which will be described later and fluorescence detecting position by the object lens.

Since the bioassay substrate 1 as stated above is formed to have circular-plate shape, it is possible to perform, by utilizing reproduction system similar to that of the optical disk system, a focusing servo control for controlling focusing position of laser beams, a positioning servo control for control of irradiation position of laser beams with respect to the radial direction and drop-position by the dropping unit, and information detecting processing for address pits 9. Namely, information contents recorded at address pits 9 and wells 8 existing in the vicinity of the address pits 9 are caused to be associated with each other to thereby read out information of the address pits 9 to irradiate laser beams only with respect to specified one well 8 to specify the position of the well 8 where fluorescence is emitted, or to control relative position between position of specific one well 8 and dropping unit, thus making it possible to drop solution with respect to the specified one well 8.

Further, in the bioassay substrate 1, there are formed region (well 8) where mutual reaction between materials for bioassay is caused to take place, and signal recording film 7 where recording/reproduction of various information is performed similarly to the optical disk. Thus, the substrate formed to have circular-plate shape can be more usefully and versatilely utilized.

For example, "information relating to the operation control of the bioassay substrate 1", "information relating to probe DNA which is changed into solid-phase state within the well 8", and "information relating to test result", etc. can be recorded onto the bioassay substrate 1.

As an actual example of information relating to the operation control of the bioassay substrate 1, there are recorded, e.g., test program in performing analysis of DNA by using the bioassay substrate 1, various data necessary for corresponding test, up-date information of test program, instruction manual of the bioassay substrate 1 and/or analyzer, and/or procedure of test processing, etc.

By recording such information relating to the operation control of bioassay substrate 1 onto the same substrate along with the region where mutual reaction between materials is caused to take place, the necessity of recording information relating to the operation control onto other recording medium to distribute it can be eliminated.

Moreover, as an actual example of information relating to probe DNA which is changed into solid-phase state within the well 8, there are recorded kind of probe DNA substances arranged at respective wells 8 and their arrangement positions, explanation of probe DNA within respective wells 8, the relationship between probe DNA and diseases, and manufacturer and/or manufacturing date of the bioassay substrate 1, etc.

By recording information relating to probe DNA which is changed into solid-phase state within such well 8 onto the same substrate where that probe DNA is changed into solid-phase state, it becomes possible to securely and easily perform management of the bioassay substrate 1.

Moreover, as a practical example of information relating to test result, there are recorded information relating to person to be tested (name, age, sex, etc.); test date, test place, person to be tested and test result data (raw data which have been read from the reaction region), DNA analysis result based on test result (visual test result data, and/or data indicating association with disease, etc.), past test results of corresponding persons to be tested (test past record or history), and other test results of corresponding persons to be tested, etc.

By recording such information relating to test results onto the same substrate in which sample DNA serving as source of test result has been caused to undergo hybridization, handling of test results becomes sure and easy.

It is a matter of course that other data may be also recorded onto the bioassay substrate 1 without being limited to information as described above.

It is to be noted that while the principal surface is divided into two regions of the recording region 3 and the reaction region 4 in the bioassay substrate 1, the recording region 3 and the reaction region 4 may overlap with each other on plane surface region. In this case, it is sufficient that position of the signal recording film 7 is formed at position remote or spaced, in a thickness direction from the reaction region 4, from depth of focus of laser beams to be irradiated in order to excite fluorescence (fluorescence of which detail will be described later), and laser beams for control (control light of which detail will be described later). Namely, this is because if the signal recording film 7 is positioned ahead of the focal point similarly to that of the two-layer (double layer) recording of the optical disc 2, laser beams are sufficiently reached to the reaction region 4.

(DNA Analyzer)

Then, a DNA analyzer 21 adapted for performing DNA analysis by using the above-described bioassay substrate 1 will be explained with reference to FIG. 5.

Figure 5:
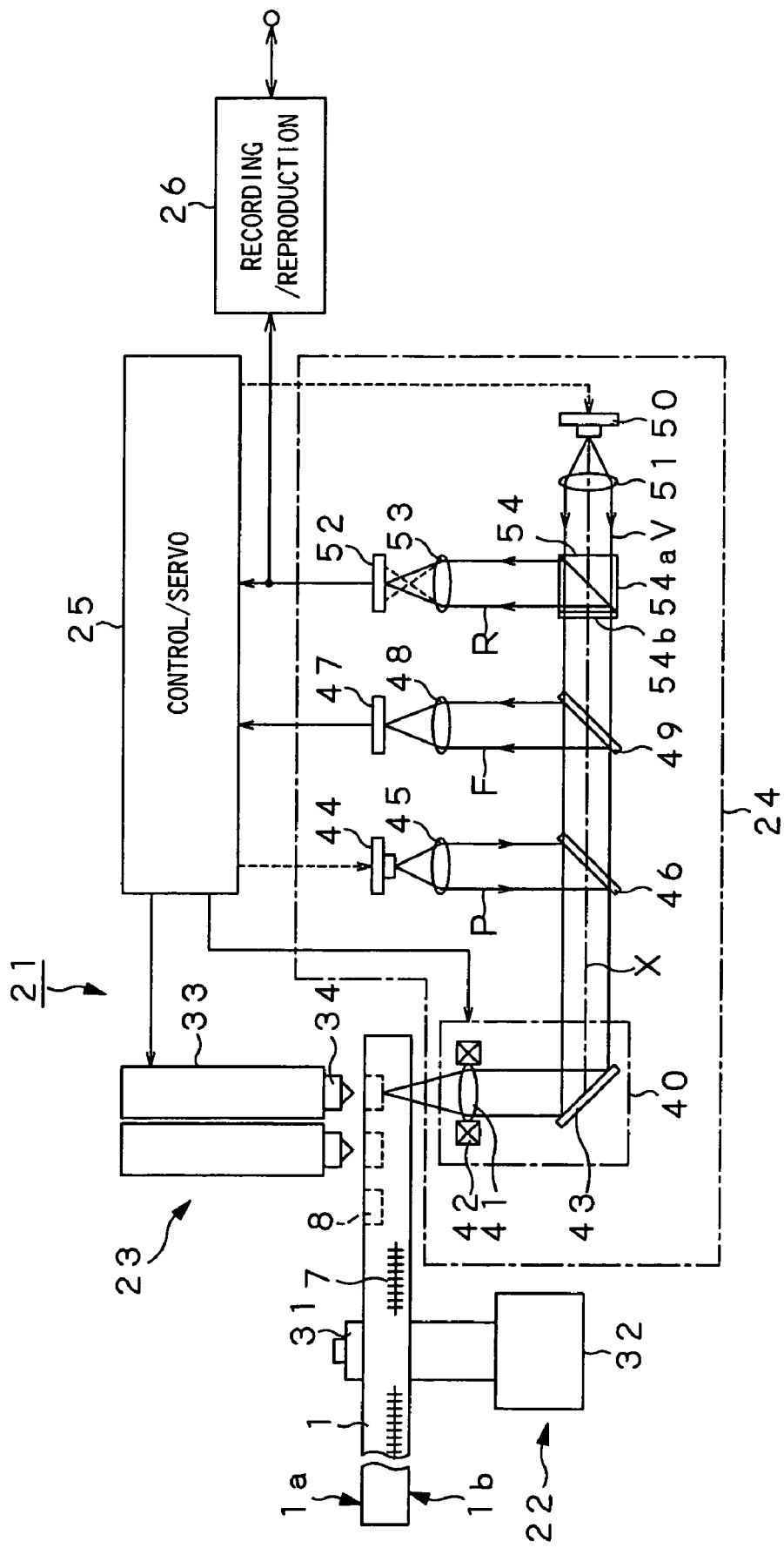
FIG. 5 is a block diagram of a DNA analyzer of the embodiment of the present invention.

The DNA analyzer 21 comprises, as shown in FIG. 5, a disk loading unit 22 for holding and rotating the bioassay substrate 1, a dropping unit 23 for storing various solutions for hybridization and for dropping the solutions into wells 8 of the bioassay substrate 1, a fluorescence detecting unit 24 for detecting fluorescence from the wells 8 of the bioassay substrate 1, a control/servo unit 25 for performing management and control of the above-mentioned respective units, and a recording/reproducing unit 26 for performing recording/reproduction of signals with respect to the signal recording film 7 of the bioassay substrate 1.

The disk loading unit 22 includes a chucking mechanism 31 adapted to be inserted into the center hole 2 of the bioassay substrate 1 to hold the bioassay substrate 1, and a spindle motor 32 for driving the chucking mechanism 31 to thereby rotate the bioassay substrate 1. The disk loading unit 22 rotationally drives the bioassay substrate 1 in the state where the bioassay substrate 1 is horizontally maintained so that the upper surface 1a side is caused to be upper direction.

The dropping unit 23 includes a storage unit 33 for storing sample solution S, and a dropping head 34 for dropping sample resolution within the storage unit 33 onto the bioassay substrate 1. The dropping head 34 is disposed above the upper surface 1a of the horizontally loaded bioassay substrate 1. Further, the dropping head 34 is caused to be of the configuration to control, in the radial direction, relative position with respect to the bioassay substrate 1 on the basis of position information and rotation synchronizing information which are read out from address pits 9 of the bioassay substrate 1 to drop sample solution S including probe DNA, sample DNA or fluorescence marking agent into a predetermined well 8 in precisely following manner.

The fluorescence detecting unit 24 includes an optical head 40. The optical head 40 is disposed at the lower side, i.e., the lower surface 1b side of the horizontally loaded bioassay substrate 1. The optical head 40 is adapted so that it can be moved in the radial direction of the bioassay substrate 1 by, e.g., sled mechanism (not shown), etc.

The optical head 40 includes an object lens 41, a biaxial actuator 42 for movably supporting the object lens 41, and a light guide mirror 43. The object lens 41 is supported by the biaxial actuator 42 so that its center axis is substantially perpendicular to the surface of the bioassay substrate 1. Accordingly, the object lens 41 can converge light beams incident from the lower side of the bioassay substrate 1 with respect to (onto) the bioassay substrate 1. The biaxial actuator 42 movably supports the object lens 41 in two directions of a direction perpendicular to the surface of the bioassay substrate 1 and radial direction of the bioassay substrate 1. By driving the biaxial actuator 42, it is possible to move focal point of light which has been converged by the object lens 41 in a direction perpendicular to the surface of the bioassay substrate 1 and in the radial direction thereof. Accordingly, in the optical head 40, it is possible to perform control operations similar to the just-focus control and the positioning control in the optical disk system.

The light guide mirror 43 is disposed at an angle of 45° relative to the optical path X thereon. The optical path X is an optical path in which fluorescence P, fluorescence F, control light V and reflected light R are incident onto the optical head 40 and are emitted therefrom. The fluorescence P and the control light V are incident from on the optical path X onto the light guide mirror 43. The light guide mirror 43 serves to allow the fluorescence P and the control light V to be reflected to refract them by 90° to allow those rays of light to be incident on the object lens 41. The fluorescence P and the control light V which have been incident on the object lens 41 are converged by the object lens 41. The rays of light thus converged are irradiated onto the bioassay substrate 1. Moreover, rays of reflected light R of the fluorescence F and the control light V are incident from the bioassay substrate 1 onto the light guide mirror 43 through the object lens 41. The light guide mirror 43 serves to allow the fluorescence F and the reflected light R to be reflected to refract them by 90° to emit those rays of light onto the optical path X. In this example, a drive signal for sled-moving the optical head 40 and a drive signal for driving the biaxial actuator 42 are given (delivered) from the control/servo unit 25.

Moreover, the fluorescence detecting unit 24 includes a fluorescence light source 44 for emitting fluorescence P, a collimator lens 45 for changing fluorescence P emitted from the fluorescence light source 44 into parallel light beams, and a first dichroic mirror 46 for refracting the fluorescence P caused to be changed into parallel light beams by the collimator lens 45 on the optical path X to irradiate refracted light beams thus obtained onto the light guide mirror 43.

The fluorescence light source 44 is light emitting means including laser light source having a wavelength for permitting the fluorescence marking agent to be excited. Fluorescence P emitted from the fluorescence light source 44 is laser beam having wavelength of 405 nm in this example. It is to be noted that, as wavelength of the fluorescence P, there may be employed any wavelength sufficient to excite the fluorescence marking agent. The collimator lens 45 changes fluorescence P emitted from the fluorescence light source 44 into parallel light beams. The first dichroic mirror 46 is a reflection mirror having wavelength selectivity, and serves to allow only light having a wavelength of the fluorescence P to be reflected, and to allow rays of light having wavelengths of fluorescence F and control light V (reflected light R thereof) to be passed therethrough. The first dichroic mirror 46 is inserted on the optical path X in a manner to have angle of 45°, and serves to allow fluorescence P emitted from the collimator lens 45 to be reflected to refract it by 90° to irradiate fluorescence P onto the light guide mirror 43.

Moreover, the florescence detecting unit 24 includes an avalanche photo-diode 47 for detecting fluorescence F, a converging lens 48 for converging fluorescence F, and a second dichroic mirror 49 for refracting fluorescence F which has been emitted from the optical head 40 onto the optical path X to irradiate the refracted light thus obtained onto the avalanche photo-diode 47.

The avalanche photo-diode 47 is a light detector having very high sensitivity, and has ability to detect fluorescence F having very few light quantity. In this example, wavelength of fluorescence F detected by the avalanche photo-diode 47 is about 470 nm. Moreover, the wavelength of the fluorescence F varies depending upon kind of the fluorescence marking agent. The converging lens 48 is a lens for converging fluorescence F onto the avalanche photo-diode 47. The second dichroic mirror 49 is inserted on the optical path X in a manner to have angle of 45°, and is disposed at the stage succeeding to the first dichroic mirror 46 when viewed from the light guide mirror 43 side. Accordingly, fluorescence F, control light V and reflected light R are incident onto the second dichroic mirror 49, but fluorescence P is not incident thereonto. The second dichroic mirror 49 is a reflection mirror having wavelength selectivity, and serves to allow only light having a wavelength of the fluorescence F to be reflected, and to allow light having a wavelength of the control light (reflected light R) to be transmitted therethrough. The second dichroic mirror 49 allows fluorescence F emitted from the light guide mirror 43 of the optical head 40 to be reflected to refract it by 90° to irradiate fluorescence F onto the avalanche photo-diode 47 through the converging lens 48.

The avalanche photo-diode 47 generates an electric signal corresponding to light quantity of fluorescence F detected in this way to deliver the electric signal thus generated to the control/servo unit 25.

Moreover, the fluorescence detecting unit 24 includes a control light source 50 for emitting control light V, a collimator lens 51 for changing control light V emitted from the control light source 50 into parallel light beams, a photo-detecting circuit 52 for detecting reflected light R of the control light V, a cylindrical lens 53 for producing astigmatism to converge reflected light R with respect to the photo-detecting circuit 52, and a light separator 54 for performing separation between the control light V and the reflected light R.

The control light source 50 is light emitting means including laser light source for emitting laser beams having, e.g., 780 nm. In this example, wavelength of the control light V is set to wavelength in which address pits 9 can be detected and recording/reproduction of information can be performed with respect to the signal recording film 7. Further, wavelength of the control light V is set to wavelength different from wavelengths of fluorescence P and fluorescence F. As wavelength of the control light F, there may be employed any wavelength which has been set as mentioned above without being limited to 780 nm. The collimator lens 51 changes control light V emitted from the control light source 50 into parallel light beams. The control light V caused to be changed into parallel light beams is incident on the light separator 54.

The photo-detecting circuit 52 includes a detector for detecting reflected light R, and a signal generating circuit for generating, from the detected reflected light R, a focus error signal, a positioning error signal, a reproduction signal of address pits 9, and a reproduction signal of the signal recording film 7. Since the reflected light R is light generated as the result of the fact that control light V is reflected on the bioassay substrate 1, its wavelength is 780 nm which is the same as that of the control light.

In this example, in the case where laser beams are irradiated onto the reaction region 4 (region of the outer circumferential side) of the bioassay substrate 1 by the optical head 40, the focus error signal results in an error signal indicating in-focus position of light converged by the object lens 32 and positional shift quantity with respect to the DNA layer 6 of the bioassay substrate 1, and the positioning error signal results in a signal indicating positional shift quantity with respect to the disk radial direction between position of a predetermined well 8 and focal point position. In the case where laser beams are irradiated onto the recording region 3 (region of the inner circumferential side) of the bioassay substrate 1 by the optical head 40, the focus error signal results in an error signal indicating positional shift quantity between in-focus position of light converged by the object lens 32 and the signal recording film 7, and the positioning error signal results in a signal indicating positional shift quantity with respect to the disk radius direction between track position of the signal recording film 7 and the focal point position.

Only in the case where laser beams are irradiated onto the reaction region 4 (region of the outer circumferential side), reproduction signal of address pits 9 is detected, and is a signal indicating information content described in the address pits 9 recorded at the bioassay substrate 1. By reading out the information content, it is possible to specify well 8 to which the control light V is irradiated at present.

Only in the case where laser beams are irradiated onto the recording region 3 (the region of the inner circumferential side), reproduction signal of the signal recording film 7 is detected, and is a signal indicating information content recorded at tracks of the signal recording film 7.

The photo-detecting circuit 52 delivers, to the control/servo unit 25, a focus error signal, a positioning error signal and a reproduction signal of address pit 9 which have been generated on the basis of reflected light R.

A cylindrical lens 53 is a lens for converging reflected light R onto the photo-detecting circuit 52, and for producing astigmatism. By producing astigmatism in this way, it is possible to generate a focus error signal by the photo-detecting circuit 52.

A light separator 54 is composed of a light separation surface 54a comprised of deflection beam splitter, and a ¼ (quarter) wavelength plate 54b. The light separator 54 has the function in which the light separation surface 54a allows light incident from the side opposite to the ¼ wavelength plate 54 to be transmitted therethrough, whereby in the case where reflected light of the transmitted light is incident from the ¼ wavelength plate 54b side, the light separation surface 54a allows it to be reflected. At the light separator 54, the light separation surface 54a is inserted on the optical path X in a manner to have angle of 45°, and is arranged at the stage succeeding to the second dichroic mirror 49 when viewed from the light guide mirror 43 side. Accordingly, the light separator 54 serves to allow control light V emitted from the collimator lens 51 to be transmitted therethrough to allow the control light V to be incident onto the light guide mirror 43 within the optical head 40, and to allow reflected light R emitted from the light guide mirror 43 of the optical head 40 to be reflected so that reflected light thus obtained is refracted by 90° to irradiate reflected light R to the photo-detecting circuit 52 through the cylindrical lens 53.

The control/servo unit 25 performs various servo control operations on the basis of a focus error signal, a positioning error signal and a reproduction signal of the address pits 9 which have been detected by the fluorescence detecting unit 24.

In the case where laser beams are irradiated onto the reaction region (region of the outer circumferential side), the control/servo unit 25 drives the biaxial actuator 42 within the optical head 40 on the basis of a focus error signal to control spacing between the object lens 41 and the well 8 to drive the biaxial actuator 42 within the optical head 40 on the basis of positioning error signal to control the positional relationship in the radial direction between the object lens 41 and the well 8 to perform sled movement control of the optical head 40 on the basis of reproduction signal of the address pits 9 to move the optical head 40 to a predetermined radial position.

In the case where laser beams are irradiated onto the recording region 3 (region of the inner circumferential side), the control/servo unit 25 drives the biaxial actuator 42 within the optical head 40 on the basis of a focus error signal to control spacing between the object lens 41 and the signal recording film 7 to drive the biaxial actuator 42 within the optical head 40 on the basis of positioning error signal to control the positional relationship in the radial direction between the object lens 41 and recording tracks of the signal recording film 7.

The recording/reproducing unit 26 performs demodulation & decoding processing of reproduction signal of data recorded at the information recording layer 7 to output data thus processed, and to perform encoding operation and modulation of recording data to be recorded into the information recording layer 7. The recording/reproducing unit 26 is supplied, at the time of reproduction, with reproduction signal outputted from the fluorescence detecting unit 24 to output demodulated and decoded data to the external. Moreover, at the time of recording, the recording/reproducing unit 26 is supplied with recording data from the external to deliver encoded and modulated data to the fluorescence detecting unit 24 to drive the control light source 50 for emitting control light V.

In the DNA analyzer 21 of the configuration as stated above, in the case where bioassay is performed, operation as described below will be performed.

Figure 6:
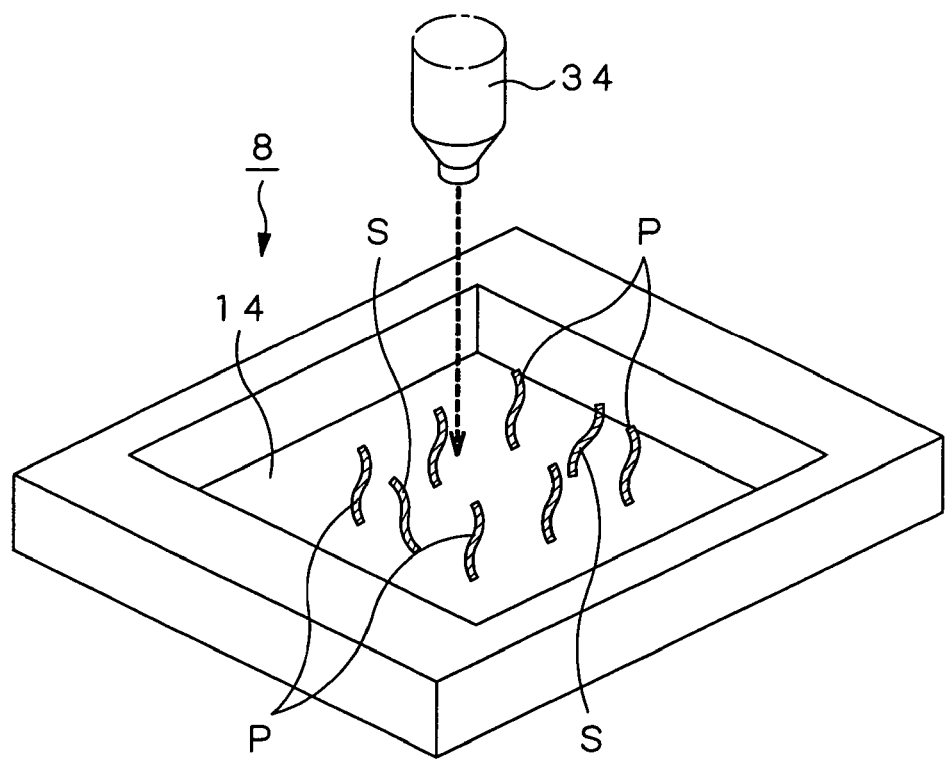
FIG. 6 is a view showing the operation when solution is dropped down with respect to well.
Figure 7:
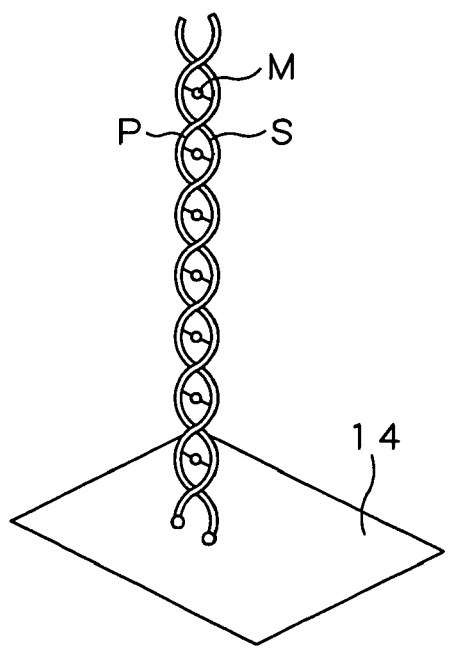
FIG. 7 is a view showing the state where fluorescence marking agent is inserted within double helix of probe DNA and sample DNA.

The DNA analyzer 21 drops solution in which sample DNA (S) is contained (included) onto the well 8 as shown in FIG. 6 while rotating the bioassay substrate 1 to perform mutual reaction (hybridization) between probe DNA (P) and sample DNA (S). Moreover, buffer solution including fluorescence marking agent M is dropped onto the bioassay substrate 1 in which hybridization processing has been completed to insert fluorescence marking agent M into double helix between probe DNA (P) and sample DNA (S) as shown in FIG. 7.

Further, the DNA analyzer 21 serves to rotate the bioassay substrate 1 where the fluorescence marking agent has been already dropped to allow fluorescence P to be incident from the lower surface 1b side of the bioassay substrate 1 to irradiate the fluorescence P onto the fluorescence marking agent within the well 8 to detect, from the lower direction of the bioassay substrate 1, fluorescence F which has been produced from the fluorescence marking agent in accordance with the fluorescence P thus irradiated.

Here, at the DNA analyzer 21, fluorescence P and control light V are irradiated onto the bioassay substrate 1 through the same object lens 41. For this reason, the DNA analyzer 21 performs focus control, positioning control and address control using the control light V, thereby making it possible to specify irradiation position of the fluorescence P, i.e., emitting position of the fluorescence F. Thus, it is possible to specify probe DNA bonded to sample DNA from light emitting position of the fluorescence thus obtained.

Further, at the DNA analyzer 21 of the configuration as stated above, at the time of recording and reproduction of data, the operation as described below will be performed.

The DNA analyzer 21 serves to stop emitting operation of fluorescence P to emit only control light V. Further, the DNA analyzer 21 performs servo control while rotating the bioassay substrate 1 to perform recording or reproduction of data with respect to tracks on the signal recording film 7.

(DNA Analysis Method)

Then, the DNA analysis method will be explained.

First, the bioassay substrate 1 is horizontally loaded (attached) to the disk loading unit 22 of the DNA analyzer 21.

Subsequently, the bioassay substrate 1 is rotated while performing position control based on address pits 9 by the DNA analyzer 21 to drop solution that probe DNA having one end modified by NCO group, etc. is contained (included) from the dropping head 34 with respect to a predetermined well 8. At this time, plural kinds of probe DNA substances are dropped with respect to a single bioassay substrate 1. In this case, one kind of probe DNA is adapted to be inserted into one well 8. It is to be noted that information indicating kind of probe DNA to be dropped into respective wells 8 is read out in advance from the signal recording film 7 such as arrangement map, etc. indicating correspondence relationship between the well and the probe DNA to perform dropping control on the basis of the arrangement map thereof.

Subsequently, electrode is inserted into solution within the well 8 from the upper surface 1a side of the bioassay substrate 1 to apply a.c. electric field having about 1 MV/m, 1 MHz to respective wells 8. When a.c. electric field is applied in this way, the probe DNA is expanded in a direction perpendicular to the bioassay substrate 1, and the probe DNA is moved in a direction perpendicular to the bioassay substrate 1 to bond modification end of the probe DNA with respect to the bottom surface 14 to which surface modification processing has been implemented in advance, thus to have ability to allow the probe DNA to be placed in solid-phase state (immobilize the probe DNA) within the well 8 (see Masao Washizu and Osamu Kurosawa: "Electrostatic Manipulation of DNA in Macrofabricated Structures", IEEE Transaction on Industrial Application Vol. 26, No. 26. P. 1165-1172 (1900)).

Subsequently, by the DNA analyzer 21, solution that the sample DNA is contained (included) is dropped from the dropping head 34 into respective wells 8 on the bioassay substrate 1 along with buffer salt.

Subsequently, the bioassay substrate 1 is transferred to thermostatic chamber, etc. after dropping of the sample DNA to heat the inside of the well 8 so that it becomes equal to several ten degrees to apply a.c. electric filed of about 1 MV/m, 1 MHz while maintaining the heated state. When such a processing is performed, the sample DNA and the probe DNA are expanded in a vertical direction so that there results less steric hindrance, and the sample DNA is move in a vertical direction with respect to the bioassay substrate 1. As a result, in the case where sample DNA and probe DNA in which mutual basic arrangements are caused to correspond to each other exist within the same well 8, those DNA substances produce hybridization.

Subsequently, after hybridization is caused to take place, fluorescence marking agent such as intercalator, etc. is dropped into the well 8 of the bioassay substrate 1 by the DNA analyzer 21. Such fluorescence marking agent is inserted into the portion between double helix between probe DNA and sample DNA in which hybridization has taken place to bond them.

Subsequently, the surface 1a of the bioassay substrate 1 is rinsed with pure water, etc. to remove the sample DNA and the fluorescence marking agent within the well 8 in which hybridization does not take place. As a result, the fluorescence marking agent is left only within the well 8 in which hybridization has taken place.

Subsequently, the bioassay substrate 1 is rotated while performing focus servo control, positioning servo control and address control using control light F by the DNA analyzer 21 to irradiate fluorescence P onto a predetermined well 8. Along with irradiation of the fluorescence P, whether or not fluorescence F is produced is detected while detecting address information.

Subsequently, the DNA analyzer 21 serves to prepare map indicating positions of respective wells 8 on the bioassay substrate 1 and presence/absence of emission of fluorescence F. Further, the DNA analyzer 21 performs analysis of the basic arrangement of sample DNA on the basis of the prepared map and arrangement map indicating probe DNA of basic arrangement dropped within respective wells 8. By referring result of this analysis, e.g., the relationship with respect to disease, etc. may be analyzed on the basis of information of the relationship between probe DNA substances and diseases which are recorded in the signal recording film 7.

Further, the DNA analyzer 21 records those analysis results and/or detected arrangement map, etc. into the signal recording film 7 of the bioassay substrate 1 to preserve them.

It is to be note that while the present invention has been described in accordance with certain preferred embodiments thereof illustrated in the accompanying drawings and described in detail, it should be understood by those ordinarily skilled in the art that the invention is not limited to embodiments, but various modifications, alternative construction or equivalents can be implemented without departing from the scope and spirit of the present invention as set forth by appended claims.

INDUSTRIAL APPLICABILITY

The bioassay substrate according to the present invention includes reaction region where mutual reaction between materials is caused to take place, and information region where signals are to be recorded. In addition, the bioassaying apparatus and bioassaying method according to the present invention are adapted to perform bioassay based on mutual reaction between materials with respect to the bioassay substrate including reaction region where mutual reaction between materials is caused to take place and information region where signals are to be recorded, and recording and/or reproduction of information are performed with respect thereto.

Thus, in the bioassay substrate according to the present invention, user is permitted to perform more variety of use. In addition, in the bioassaying apparatus and the bioassaying method according to the present invention, it is possible to use circular-plate shaped bioassay substrate in more variety manner.

The invention claimed is:

1. A bioassaying apparatus for performing bioassay based on a reaction between probe material and sample material, the bioassaying apparatus comprising:

a substrate holder for holding and rotationally driving a substrate for bioassay, the substrate including a reaction region and an information region, the reaction region being formed on an upper layer of the substrate, and the information region being formed on a lower layer of the substrate, the reaction region being adapted so that the sample material and fluorescence marking agent are permitted to be dropped from an upper side of the substrate and the probe material is permitted to be immobilized on the upper layer, the reaction region serving as a field of mutual reaction between the probe material and the sample material, the reaction region receiving a laser beam with respect to the fluorescence marking agent from a lower side of the substrate, and the information region receiving light from the lower side of the substrate to record and/or reproduce information contained in the information region, wherein the lower layer is spaced from the upper layer in a thickness direction by at least a depth of focus of the laser beam;

a fluorescence detection optical system for irradiating the laser beam having a first wavelength with respect to the reaction region of the substrate to detect fluorescence having the first wavelength produced from the fluorescence marking agent in accordance with the laser beam; and an information recording/reproducing optical system for irradiating the light having a second wavelength with respect to the information region of the substrate.

2. The bioassaying apparatus as set forth in claim 1, wherein the substrate is circular-plate shaped, and the substrate holder rotationally drives the circular-shaped substrate.

\* \* \* \* \*

UNITED STATES PATENT AND TRADEMARK OFFICE
CERTIFICATE OF CORRECTION

PATENT NO. : 7,718,129 B2 Page 1 of 1
APPLICATION NO. : 10/559745
DATED : May 18, 2010
INVENTOR(S) : Takayoshi Mamine et al.

It is certified that error appears in the above-identified patent and that said Letters Patent is hereby corrected as shown below:

On the Title Page, Item (57), in the Abstract, line 13, "filed" should read --field--.

Signed and Sealed this

Tenth Day of August, 2010

David J. Kappos
*Director of the United States Patent and Trademark Office*